United States Patent [19]
Ingram

[11] Patent Number: 5,928,936
[45] Date of Patent: Jul. 27, 1999

[54] CELL CULTURE CONTAINER THAT SELF-SEALS AFTER CANNULA PENETRATION MADE OF POROUS SHEETS

[75] Inventor: Marylou Ingram, Pasadena, Calif.

[73] Assignee: Huntington Medical Research Institutes, Pasadena, Calif.

[21] Appl. No.: 08/838,704

[22] Filed: Apr. 9, 1997

[51] Int. Cl.[6] .............................. C12M 3/00; C12N 5/00; C12N 5/06; A01N 63/00

[52] U.S. Cl. .................. 435/297.1; 424/93.7; 435/283.1; 435/394; 435/395

[58] Field of Search .................. 424/93.7; 435/283.1, 435/297.1, 383, 394, 395, 403

[56] References Cited

U.S. PATENT DOCUMENTS

| | | | |
|---|---|---|---|
| 4,224,413 | 9/1980 | Burbidge | 435/284 |
| 4,496,362 | 1/1985 | Leurink | 604/408 |
| 4,604,360 | 8/1986 | Hounsell | 435/287 |
| 5,282,861 | 2/1994 | Kaplan | 623/16 |
| 5,374,264 | 12/1994 | Wadsworth, Jr. | 604/414 |
| 5,523,228 | 6/1996 | Ingram et al. | 435/240.25 |
| 5,620,420 | 4/1997 | Kriesel | 604/133 |

OTHER PUBLICATIONS

Tantalum Foams for Cancellous Bone Implants, dated Mar. 1993 by Richard B. Kaplan, et al.
Canine Studies of Bone Ingrowth with Implex Corporation Tantalum Porous Implants, Progress Report, dated Jun. 27, 1995, by J.D. Bobyn, Ph.D., et al.

*Primary Examiner*—David M. Naff
*Attorney, Agent, or Firm*—Christie, Parker & Hale, LLP

[57] ABSTRACT

A container for growing cells in a culture medium is made by sealing two sheets of gas-permeable elastomeric material such as made of silicone together to enclose a culture chamber. A portion of one of the sheets is in the shape of a dome having a wall extending transverse to a major plane of that sheet. The thickness of the wall is greater than the thickness of the rest of the sheet. A permeable and porous body, preferably coated with a thin film of metal, may be in the culture chamber to provide a substrate for three-dimensional growth. A porous body can be implanted in an organ of an animal to allow dividing cells to grow into the porous body. The porous body is removed from the animal and placed in contact with other porous bodies in the culture chamber where cells grow from the porous body containing cells into the other porous bodies. Thereafter, the chamber can be opened and each body with cells combined with additional porous bodies so that additional cells can be grown to provide an almost unlimited source of cells from having started with the organ of only one animal.

11 Claims, 2 Drawing Sheets

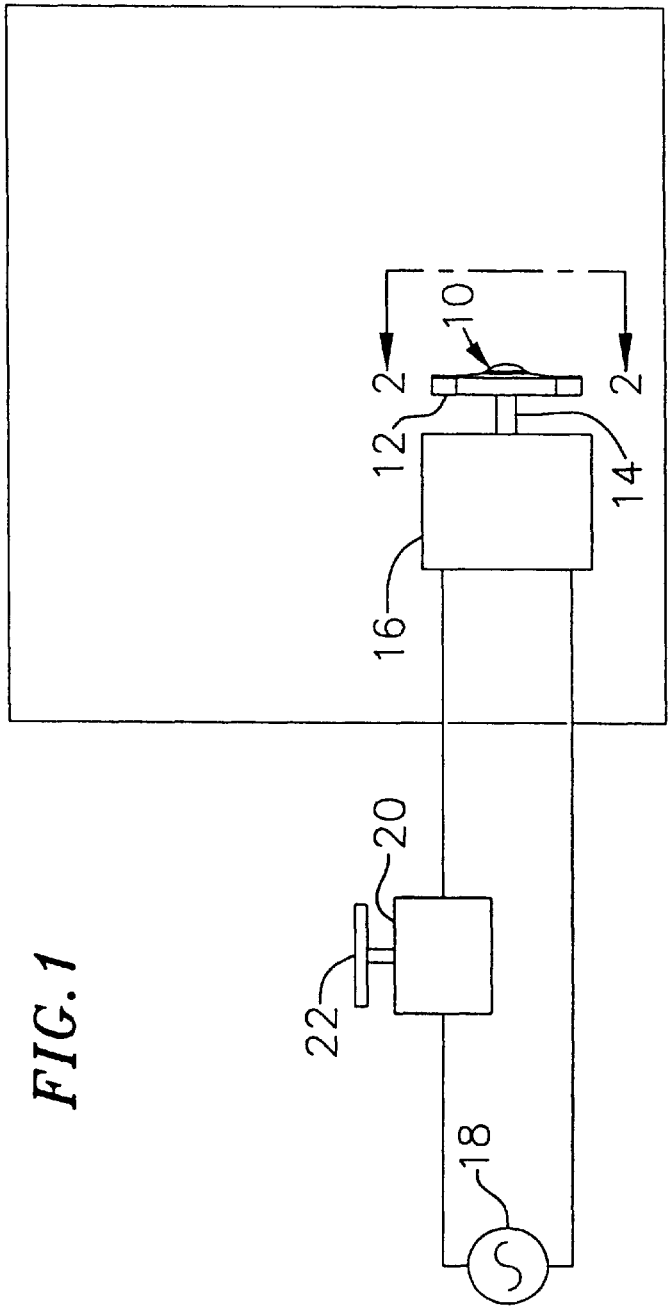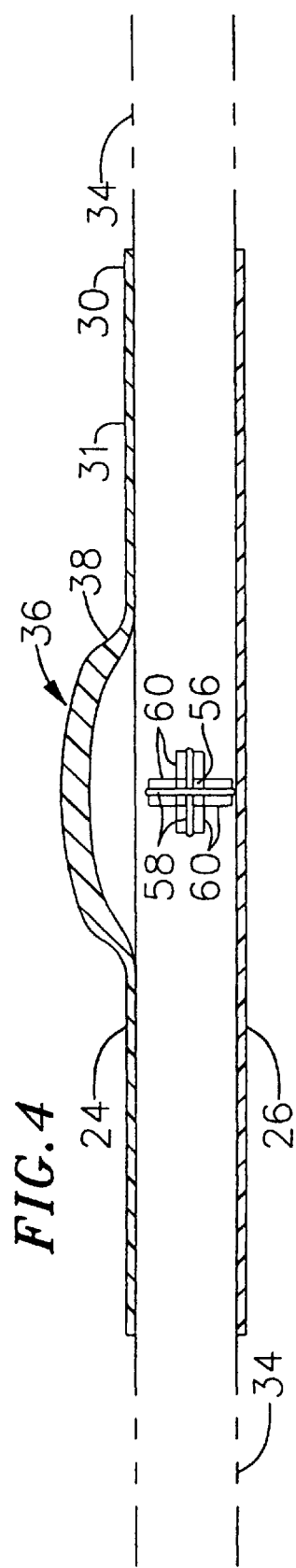

CELL CULTURE CONTAINER THAT SELF-SEALS AFTER CANNULA PENETRATION MADE OF POROUS SHEETS

BACKGROUND OF THE INVENTION

The art and science of cell and tissue culture has evolved continuously since 1897, when Loeb demonstrated that cells of the blood and connective tissue can be maintained in a viable state in vitro. Methods have been developed to study various differences in cells and tissues grown in semi-solid media as contrasted with growth in liquid media. Similar studies have been made of differences in growth and function of cells and tissues in liquid which is stirred and in liquid which is quiescent.

Many types of cells and tissues grown in quiescent liquid cultures develop as monolayers, which are less representative of three-dimensional structures for cells and tissues which occur naturally in animals. Investigators studying the effects of chemotherapeutic agents and ionizing radiation on cancer cells have recognized the importance of culturing cells as three-dimensional structures that correspond to micro-lesions in vivo. Extensive basic studies of multicellular growths have shown that cells and tissues grown under conditions which favor three-dimensional structures are more useful than monolayer-grown cells. For example, cells grown as three-dimensional structures may express genes that are silent in monolayer-grown cells. Thus, three-dimensional structures are proving useful in studies of differentiation, immunology and molecular genetics.

U.S. Pat. No. 5,523,228 issued Jun. 4, 1996 to Ingram et al. discloses improved methods and apparatus for generating cell and tissue cultures which have the desired three-dimensional structure. That patent discloses injecting a mixture of liquid culture medium and cells to be grown into a flexible container or bag which is permeable to oxygen and carbon dioxide. The culture medium and cells are introduced into the bag with a hypodermic syringe through a conventional hypodermic syringe port (with a female Luer lock) sealed between two gas-permeable sheets which form the walls of the bag. The bag is completely filled with the mixture and slowly rotated about a horizontal axis to keep the cells suspended under low-shear hydrodynamic flow. Metabolized culture medium is removed and replaced with fresh medium as required from time to time by using a hypodermic syringe connected to the syringe port.

The apparatus disclosed in U.S. Pat. No. 5,523,228 produces cells with the desired three-dimensional structure, but suffers the disadvantage that the hypodermic syringe port introduces an irregularity to the interior surface of the bag, which traps cells and creates excessive localized turbulence, which interferes with three - dimensional cell growth. Moreover, the hypodermic syringe port makes it difficult and time-consuming to remove all air bubbles from the chamber when filling it with liquid culture medium and cells. As explained in the patent, it is important to fill the chamber completely (zero head space) because air bubbles increase hydrodynamic shear and turbulence, which discourages desired three-dimensional growth.

SUMMARY OF THE INVENTION

This invention provides an improved container for growing cells with a three-dimensional structure by eliminating the conventional hypodermic syringe port, such as the type associated with standard intravenous tubing, and disclosed in the Ingram et al. patent referred to above. The container of this invention is free of any irregular internal surface, thereby promoting desired cell growth, and facilitating complete filling of the chamber with a cannula connected to a hypodermic syringe.

In terms of apparatus for growing cells in a culture medium, this invention provides a container which includes a gas-permeable first sheet made of elastomeric material. A gas-permeable second sheet is secured to the first sheet to form an enclosed culture chamber. A first portion of the first sheet which encloses one part of the chamber is substantially thicker than a second portion of a first sheet which encloses another part of the chamber. The thickness of the first portion of the first sheet is sufficient to effect self-sealing, even after repeated penetration with a cannula.

In the preferred container of this invention, the first and second sheets each have a respective major plane, and the sheets are disposed with the major planes substantially parallel. A portion of the first sheet which encloses the chamber is displaced away from the second sheet to form a cavity with a wall section extending transverse to the major planes. The wall section is sufficiently thick to effect self-sealing, even after being repeatedly penetrated by the cannula.

Preferably, the two sheets are made of silicone, and the thickness of each sheet is between about 0.1 and about 1 mm. The thickness of the wall section of the displaced portion of the first sheet is between about 3 mm and about 6 mm thick.

In another preferred form of the invention, a biocompatible porous and permeable body is disposed within the culture chamber to provide a substrate for cells grown in the culture medium. Preferably, the porous and permeable body is a carbonaceous skeleton, which may be coated with a film of metal selected from the group consisting of tantalum, niobium, hafnium, and tungsten, or an alloy of two or more of those metals.

In terms of method for growing living cells, the invention includes implanting a first porous and permeable body in a living organ such as the liver of a mouse. The organ contains dividing cells, which grow into the implanted body. Thereafter, the first body with the living cells is removed from the organ, and placed in contact with a second porous and permeable body in a culture medium so that living cells grow from the first body into the second body. This procedure is repeated as many times as desired to grow an unlimited amount of cells from the relatively limited number of cells taken from the organ. This procedure is particularly useful in generating new organs from a type of organ which has only a limited number of dividing cells, such as the liver of a mammal. Preferably, the body with the cells taken from the organ are grown in a culture medium confined and rotated in a container as described above.

DESCRIPTION OF THE DRAWINGS

FIG. 1 shows the container of this invention mounted for rotation about a horizontal axis;

FIG. 4 is a sectional elevation of the first and second sheets in position to be sealed together and form a chamber which includes a group of porous bodies secured together.

DETAILED DESCRIPTION OF THE INVENTION

Figure 2:
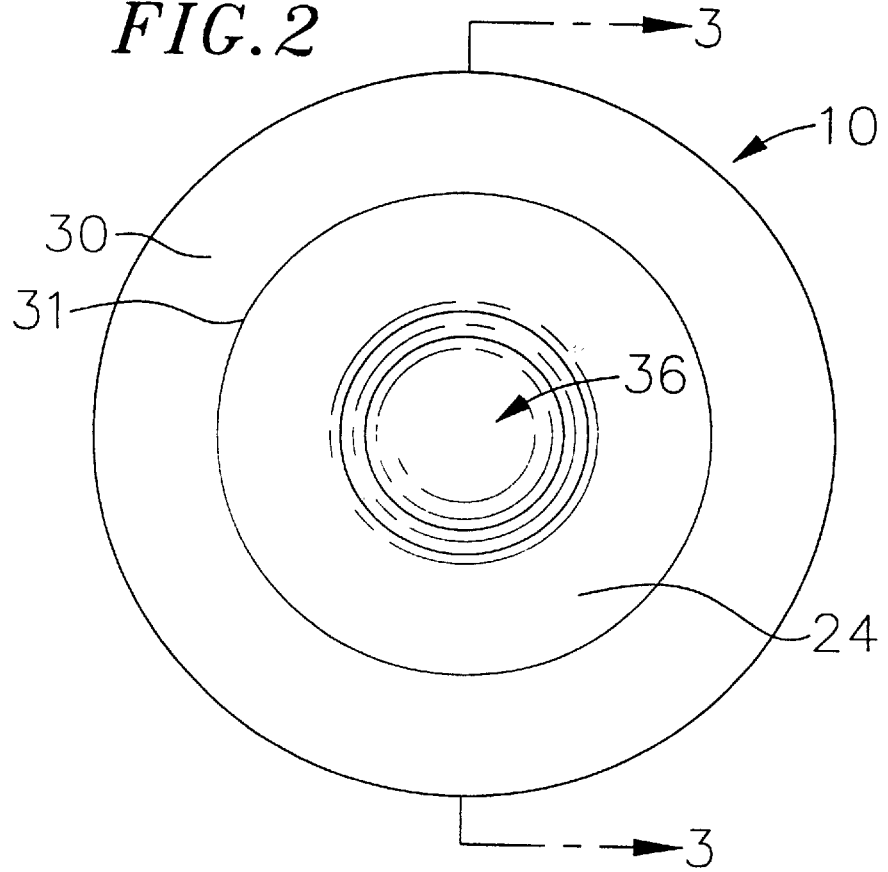
FIG. 2 is a view taken on line 2—2 of FIG. 1.
Figure 3:
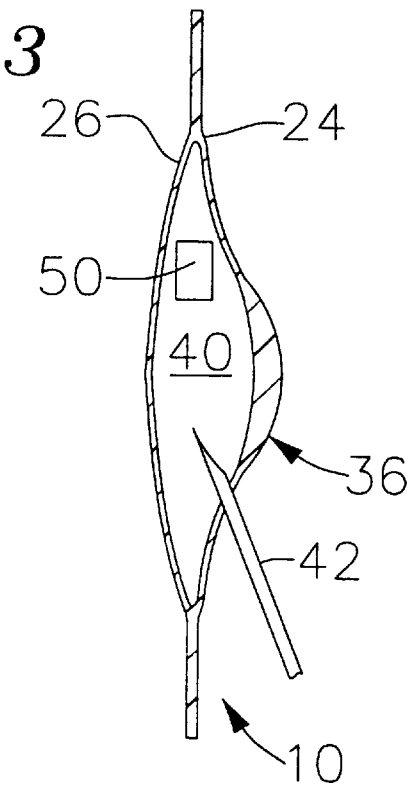
FIG. 3 is a view taken on line 3—3 of FIG. 2.

Referring to FIGS. 1, 2 and 3, a container 10 is strapped to one face of a vertical disk 12 mounted on a horizontal shaft 14 of an electric motor 16. A power supply 18 is connected through a variable transformer 20 to the motor so the speed of the shaft can be set by a control knob 22 on the variable transformer.

As shown best in FIGS. 2, 3 and 4 the container includes first and second congruent circular sheets 24, 26, respectively. The sheets are molded from an elastomeric material, such as silicone, which is permeable to oxygen and carbon-dioxide and impermeable to a liquid culture medium (not shown), which may be of conventional type. The sheets are sealed together around their respective circumferences in an annular zone 30 (FIG.2) having a width equal to about one sixth of the diameter of the sheets, as indicated by dotted line 31. The sealing is effected by any suitable means, such as, with an adhesive, or by heat sealing. An enclosed culture chamber 40 is formed between the unsealed central portions of the sheets.

FIG. 4 shows the first and second sheets positioned just before being sealed together to form the container. Each sheet normally lies in respective parallel major planes 34. The first and second sheets are molded to be flat, except for a dome-shaped portion 36 in the center of the first sheet. The dome-shaped portion is displaced from the major plane of the first sheet in a direction away from the second sheet. The inner surface of the dome-shaped portion 36 is concave towards the second sheet, and lies in part of a first sphere (not shown). The outer surface of the dome-shaped portion 36 is convex away from the second sheet, and lies in part of a second sphere (not shown) having a radius shorter than that of the first sphere. The respective centers of the first and second spheres lie on a straight line (not shown) perpendicular to the two major planes of the sheet, and which passes through the center of the dome. Thus, the dome-shaped portion has a continuous annular wall 38 which extends transverse to the major planes of the two sheets, and which has a thickness that increases with distance from the second sheet.

The first and second sheets are of the same thickness, except for the dome-shaped portion of the first sheet. In a typical container, the first and second sheets are between 0.1 mm and about 1.0 mm thick, and the maximum thickness of the dome wall is between about 2 mm and about 6 mm. Preferably, the part of the dome wall is at least 3 times thicker than the flat portion of the first sheet.

As shown best in FIGS. 3 and 4, the inner surface of the first sheet makes a smooth transition with the periphery of the domed shaped portion so as not to present any sharp corners or irregular surfaces, which would create excessive turbulence or provide traps for cells as the container is rotated.

After the two sheets are sealed together to form the enclosed culture chamber as shown in FIG. 3. The chamber is autoclaved to sterilize it, and then filled by piercing the dome with a hypodermic needle (cannula) 42 secured to a conventional hypodermic syringe (not shown), which contains a mixture (not shown) of liquid culture medium and cells to be grown. The mixture fills the chamber to the slightly distended position shown in FIG. 3. Preferably, the container is held with the major planes of the sheet substantially horizontal so that the dome portion of the container is at the highest point. This causes air or other gas trapped in the container to accumulate under the dome in a slightly compressed state under the pressure established by the force used to inject liquid culture medium into the container. All gas trapped within the container is removed by positioning the sharp end of the cannula adjacent the thickest portion of the dome, and relaxing pressure on the hypodermic syringe plunger, or withdrawing the syringe plunger, so gas flows out of the chamber and into the cannula. The syringe is elevated slightly so gas flows up through liquid remaining in the barrel of the syringe. This procedure is repeated as many times as necessary until all of the gas phase within the chamber is removed.

As shown in FIGS. 3 and 4, the transverse wall of the dome makes it easy to insert the sharp of the point of the cannula through the dome wall at a relatively shallow angle with respect to the major planes of the sheets, thereby avoiding penetration of the second sheet. Thus, the chamber can be quickly and easily filled completely with the mixture of liquid culture medium and cells so that no air bubbles are left trapped in the chamber to cause undesired turbulence during subsequent rotation of the container.

The sheets used to make the container of this invention can be of any suitable elastomeric material which is permeable to oxygen and carbon dioxide, and which is self-sealing, even after being repeatedly penetrated with a hypodermic syringe cannula. The presently preferred silicone sheets are obtained from Medtronic PS Medical at 125-B, Cremona Drive, Goleta, Calif. 93117. According to the data furnished by the manufacturer, the permeability of the silicone sheets having a thickness of 25 $\mu$m, at 25° C. for carbon dioxide is greater than $25.9 \times 10^3$ cm$^3$/m$^2$/24 hr/atm, and for oxygen is greater than $11.6 \times 10^3$ cm$^3$/m$^2$/24 hr/atm. The sheets are preferably clear so complete filling can easily be accomplished, and the cultures inspected by direct vision or microscopy.

The liquid culture medium or media and cells are handled in the same manner and may be of the same type as those disclosed in U.S. Pat. No. 5,523,228 to Ingram et al., the entirety of which is incorporated herein by reference.

Although the container of this invention can be of any shape or size, a useful size includes sheets which have a diameter of about 72 mm, an annular sealing band of about 12 mm, an unsealed annular band of about 12 mm, and a dome shaped portion having a maximum diameter of about 25 mm. The interior surface of the dome is displaced from the major plane of the first sheet by a distance of about 5 mm, and a maximum thickness of the dome wall is about 4 mm.

For those types of cells whose growth is encouraged by contact with a supporting surface, a porous and permeable body 50 (FIG.3) is disposed within the culture chamber before the two sheets are sealed together. The porous body can be of any desired shape, but conveniently is a small cube between about 2 mm and about 5 mm per edge, and is made of a carbonaceous biocompatible material such as that disclosed in U.S. Pat. No. 5,282,861 to Kaplan. The disclosure of that patent is incorporated in its entirety herein. In brief, the body 50 is a continuous channels. The pore sizes are between about 10 $\mu$m and about 150 $\mu$m. The carbonaceous body can be used by itself, but it can be made stronger and more easily machined to different shapes by depositing a thin film of metallic material on the carbonaceous body to cover substantially all the interconnecting network, and thus form a sturdy composite porous and permeable biocompatible material. The thin film of metal can be tantalum, niobium, hafnium, or tungsten, or alloys of any two or more of those metals. The porous body coated with a film of tantalum can be purchased from Ultramet at 12173 Montague Street, Pacoima, Calif. 91331.

With the body disposed in the culture medium with appropriate cells, and the container slowly rotated as described in U.S. Pat. No. 5,523,228, the cells grow on and within the body in a three-dimensional structure which more nearly approximates that achieved in nature than if the cells were grown without rotation.

In yet another form of the invention, a relatively small cube of the body 50 described with respect to FIG. 3 is implanted in an organ (not shown), say the liver of a mammal, such as a mouse, to allow dividing liver cells to grow into the body, and produce cell structure which approximates that of the natural liver.

In a further embodiment, once the liver cells grow into the porous body, the body is removed and placed in contact with other porous bodies. For example, referring to FIG. 4, a first body 56 in the shape of a cube, which has been implanted in the liver of a mammal and which contains liver cells grown into it, is secured by ligatures 58 to 4 cubes of porous bodies 60 of the same size as the first body 56, and placed on a second sheet 26. If desired, two additional cubes of porous bodies (not shown) can be secured to the first body 56, so each face of body 56 is in contact with a respective matching face of bodies 60. Thereafter, a first sheet 24 is sealed to the second sheet to provide a culture chamber in which additional cells can grow from the first body 56 and into the additional bodies 60. Thereafter, the culture chamber can be opened, and each body with cells mounted as just described with additional porous bodies so that additional cells can be grown to provide an almost unlimited source from having started with the organ of only one animal. This provides an inexpensive and convenient way of obtaining cell and tissue cultures for in vitro scientific observations and experiments.

I claim:

1. A culture container for growing cells in a culture medium, the container comprising:

a gas-permeable continuous first sheet having a major plane, the first sheet being made of an elastomeric material;

a gas-permeable second sheet having a major plane, the two sheets being secured together with the major planes substantially parallel and to form an enclosed culture chamber between them, a portion of the first sheet which encloses the chamber being formed integrally with the first sheet to make a smooth transition with the rest of the first sheet and be displaced away from the major plane of the first sheet and away from the second sheet to form a dome-shaped cavity with a wall section extending transverse to the major planes, said portion of the first sheet being sufficiently thick to effect self-sealing after being repeatedly penetrated by a cannula, the thickness of said portion of the first sheet being substantially greater than the thickness of the rest of the first sheet.

2. The container according to claim 1 in which the first sheet is made of silicone.

3. The container according to claim 1 in which both sheets are made of silicone.

4. The container according to claim 1 in which the thickness of said portion of the first sheet is substantially greater than the thickness of the rest of the first sheet, and of the thickness of the second sheet.

5. The container according to claim 1 in which the thickness of said portion of the first sheet is between about 3 mm and about 6 mm, and the thickness of each of the sheets is between about 0.1 mm and about 1 mm.

6. The container according to claim 1 in which the thickness of said portion of the first sheet increases with distance from the major planes.

7. The container according to claim 1 in which a porous and permeable body is disposed within the culture chamber to provide a substrate for cells grown in the culture medium.

8. The container according to claim 7 in which the body is carbonaceous.

9. The container according to claim 8 in which the body is coated with a film of metal selected from the group consisting of tantalum, niobium, hafnium, and tungsten, or an alloy of two or more of those metals.

10. The container according to claims 1, 7 or 8 in which the portion of the first sheet displaced away from the second sheet is generally hemispheric in shape, with a concave surface facing the second sheet.

11. The container according to claim 1 in which the thickness of said portion of the first sheet is at least 3 times thicker than the rest of the first sheet.

* * * * *